(12) United States Patent
Asao et al.

(10) Patent No.: US 10,376,151 B2
(45) Date of Patent: Aug. 13, 2019

(54) SYSTEM AND METHOD FOR PREVENTING DIRECTLY IRRADIATING ACOUSTIC WAVE DETECTOR FOR PHOTOACOUSTIC IMAGING

(71) Applicant: CANON KABUSHIKI KAISHA, Tokyo (JP)

(72) Inventors: Yasufumi Asao, Kyoto (JP); Takuji Oishi, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 807 days.

(21) Appl. No.: 14/775,767

(22) PCT Filed: Feb. 18, 2014

(86) PCT No.: PCT/JP2014/054250
§ 371 (c)(1),
(2) Date: Sep. 14, 2015

(87) PCT Pub. No.: WO2014/156408
PCT Pub. Date: Oct. 2, 2014

(65) Prior Publication Data
US 2016/0022149 A1 Jan. 28, 2016

(30) Foreign Application Priority Data
Mar. 26, 2013 (JP) .................. 2013-064511

(51) Int. Cl.
*A61B 5/00* (2006.01)
*A61B 5/107* (2006.01)

(52) U.S. Cl.
CPC .......... *A61B 5/0095* (2013.01); *A61B 5/0077* (2013.01); *A61B 5/1077* (2013.01); *A61B 5/742* (2013.01)

(58) Field of Classification Search
CPC .................................................. A61B 5/0095
See application file for complete search history.

(56) References Cited

U.S. PATENT DOCUMENTS 7,864,307 B2  1/2011  Fukutani et al. ............... 356/73
8,864,667 B2  10/2014 Asao et al. .................... 600/437
(Continued)

FOREIGN PATENT DOCUMENTS

JP  A 2010-094181  4/2010
JP  A 2010-259604  11/2010
(Continued)

OTHER PUBLICATIONS

K. Fukutani et al., "Dual Illumination Mode Photoacoustic Tomography for Quantitative Imaging", *IEEE Ultrasonics Symposium*, 2010.

Primary Examiner — James M Kish
(74) Attorney, Agent, or Firm — Venable LLP

(57) ABSTRACT

Provided is an object information acquiring apparatus including: a light source; a controller that controls irradiation of light from the light source; a detector that receives an acoustic wave generated from an object onto which light from the light source is irradiated; a processor that generates characteristic information inside the object using the acoustic wave received by the detector; and an acquirer that acquires the shape of the object, wherein the controller controls an irradiation area when light is irradiated from the light source onto the object, based on the shape of the object acquired by the acquirer.

11 Claims, 8 Drawing Sheets

(56) References Cited

U.S. PATENT DOCUMENTS

| | | | |
|---|---|---|---|
| 8,991,261 B2 | 3/2015 | Asao | 73/655 |
| 9,330,462 B2 | 5/2016 | Oishi | G06T 7/0014 |
| 2006/0258939 A1 | 11/2006 | Pesach et al. | 600/438 |
| 2010/0053618 A1* | 3/2010 | Nakajima | A61B 5/0059 356/432 |
| 2010/0087733 A1 | 4/2010 | Nakajima et al. | 600/437 |
| 2010/0284591 A1* | 11/2010 | Arnon | A61B 5/015 382/128 |
| 2010/0324422 A1 | 12/2010 | Wanda et al. | 600/443 |
| 2011/0263963 A1* | 10/2011 | Nanaumi | A61B 5/0073 600/407 |
| 2012/0127557 A1 | 5/2012 | Masumura et al. | 359/291 |
| 2013/0031982 A1 | 2/2013 | Sato et al. | 73/655 |
| 2013/0267823 A1 | 10/2013 | Nakajim et al. | 600/407 |
| 2014/0018645 A1 | 1/2014 | Wada et al. | 600/316 |
| 2014/0046166 A1 | 2/2014 | Tokita | 600/407 |
| 2014/0051971 A1 | 2/2014 | Tokita | 600/407 |
| 2014/0058245 A1 | 2/2014 | Oishi et al. | 600/407 |

FOREIGN PATENT DOCUMENTS

| | | |
|---|---|---|
| JP | A 2012-231978 | 11/2012 |
| JP | A 2012-231980 | 11/2012 |
| JP | A 2013-048671 | 3/2013 |
| WO | WO 2012/157221 A1 | 11/2012 |
| WO | WO 2013/031586 A | 3/2013 |

\* cited by examiner

SYSTEM AND METHOD FOR PREVENTING DIRECTLY IRRADIATING ACOUSTIC WAVE DETECTOR FOR PHOTOACOUSTIC IMAGING

TECHNICAL FIELD

The present invention relates to an object information acquiring apparatus and a control method thereof.

BACKGROUND ART

Lately research on a photoacoustic diagnostic apparatus that acquires biological function information utilizing the photoacoustic effect is progressing as an apparatus that images inside the organism non-invasively in the medical field. The photoacoustic effect is a phenomena where an acoustic wave is generated when pulsed light is irradiated onto an object, due to the absorption of the light propagated and diffused inside the object. The photoacoustic diagnostic apparatus detects a time-based change of the generated acoustic wave at a plurality of locations, mathematically analyzes, in other words, reconstructs the acquired signals, and three-dimensionally visualizes information related to the optical characteristic values inside the object. Thereby an internal tissue, which is a generation source of the generated acoustic wave, is imaged. One reconstruction method is the back projection method. Back projection is a calculation method where each reception signal is propagated in reverse and superimposed to specify a signal source, considering the propagation velocity of the sound inside the object. If near infrared light is used for the pulsed light, blood vessel images can be easily generated since the near infrared light can easily transmit through water, which constitutes most of an organism, and is easily absorbed by hemoglobin in the blood. Further, oxygen saturation in the blood, which is functional information, can be measured by comparing blood vessel images generated using pulsed light of different wavelengths. Since the oxygen saturation of the blood around a malignant tumor is assumed to be lower than that of the blood around a benign tumor, it is expected that a malignant/benign tumor can be distinguished by knowing the oxygen saturation.

As Expression (1) shows, the intensity p of a photoacoustic wave depends on the intensity $\phi$ of light that reaches the light absorber.

$$p = \Gamma \cdot \phi \cdot \mu_a \quad (1)$$

Here $\Gamma$ is a Grüneisen constant and $\mu_a$ is a light absorption coefficient. As Expression (1) shows, even if the light absorption coefficient of the light absorber is a large value, the intensity of the acoustic wave to be generated is low if low quantity light reaches the light absorber. Whereas even if the light absorption coefficient is not so large, the intensity of the acoustic wave to be generated is high if a high quantity of light reaches the light absorber.

A configuration applying this principle has been proposed. Patent Literature 1 is a configuration of disposing a reflection member on a surface of a photoacoustic detector. Non-patent Literature 1 is a configuration of irradiating light onto an object from a plurality of directions.

CITATION LIST

Patent Literature

PTL 1: US Patent Application Publication No. 2010/0053618

Non-Patent Literature

NPL 1: Fukutani et al., Proc. IEEE Ultrason. Symp., P5-M2-5 (2010)

SUMMARY OF INVENTION

Technical Problem

In a photoacoustic diagnostic apparatus, the following problem occurs if the positional relationship of a pulsed light source, an object, and an acoustic wave detector is in a sequence of "pulsed light source-object-acoustic wave detector".

The size of the diagnostic apparatus is determined to be relatively large assuming that various sized objects are diagnosed. Therefore in the case of diagnosing an object smaller than the maximum size that is expected, the sequence of the above mentioned positional relationship may become "pulsed light source-(blank)-acoustic wave detector" depending on the area. In other words, in an area where the object does not exist, light is directly irradiated onto the surface of the acoustic wave detector. In some cases the pulsed light may still be irradiated onto the acoustic wave detector due to reflection or the like, even if the positional relationship is in a different sequence. If the pulsed light is irradiated directly onto the acoustic wave detector, a photoacoustic wave is generated because of light absorption by the acoustic wave detector itself. In the following description, such signals from an area other than the object to be measured are called "noise".

To decrease this noise, it is necessary to decrease the quantity of light absorbed by the acoustic detector. Hence according to Patent Literature 1, a reflection member is installed on the surface of the acoustic wave detector, so as to decrease the light absorbed through the surface of the acoustic wave detector. Thereby the quantity of light absorbed by the acoustic detector is decreased, and noise can be reduced. According to Patent Literature 1, a configuration where the pulsed light irradiated from the light source is directly reflected onto the acoustic wave detector is not used, but a configuration, where light irradiated onto an organism and diffused inside the organism is irradiated from the organism and is reflected on the front surface of the acoustic detector, is used.

The method disclosed in Patent Literature 1 is to a certain degree effective, but in the case of the above mentioned sequence of the positional relationship "pulsed light source-object-acoustic wave detector", light is directly irradiated onto the surface of the acoustic wave detector in an area where the object does not exist. Thus the influence of noise generated by direct irradiation of light onto the acoustic wave detector can be a problem, even if the light absorption coefficient of the acoustic wave detector is small. Particularly when an object has a thickness over several cm, the quantity of pulsed light must be increased to measure a deep region thereof. In such a case the obvious influence of noise appears.

The light instantaneously reaches the acoustic wave detector and the object, and generates an acoustic wave almost simultaneously. The acoustic wave, on the other hand, requires transfer time, which is determined depending on the sound velocity of the medium and the transfer distance. Therefore after the pulsed light is irradiated, the acoustic wave detector first receives a strong signal (noise originated from the photoacoustic effect of the acoustic wave detector itself), and then receives a signal from an area inside the object (information to be imaged) before a response to the signal completes. This means that it is difficult to separate these two signals based on time. Further, artifacts which originated from a strong signal from an area outside the object are superimposed on an image reconstructed using this signal.

With the foregoing in view, it is an object of the present invention to provide a technique to suppress noise that originated from an acoustic wave generated from an area other than an object, and to acquire a high quality image in the photoacoustic diagnosis.

Solution to Problem

The present invention provides an object information acquiring apparatus, comprising:
a light source;
a controller configured to control irradiation of light from the light source;
a detector configured to receive an acoustic wave generated from an object onto which light from the light source is irradiated;
a processor configured to generate characteristic information inside the object using the acoustic wave received by the detector; and
an acquirer configured to acquire a shape of the object, wherein
the controller controls an irradiation area when light is irradiated from the light source onto the object, based on the shape of the object acquired by the acquirer.

The present invention also provides a control method of an object information acquiring apparatus including a light source, a controller configured to control irradiation of light from the light source, a detector, a processor and an acquirer, the control method comprising:
a step of the acquirer acquiring the shape of an object;
a step of the controller controlling an irradiation area when light is irradiated from the light source onto the object, based on a shape of the object acquired by the acquirer;
a step of the detector receiving an acoustic wave generated from the object onto which light from the light source is irradiated; and
a step of the processor generating characteristic information inside the object using the acoustic wave received by the detector.

Advantageous Effects of Invention

The present invention provides a technique to suppress noise that originated from an acoustic wave generated from an area other than an object to acquire a high quality image in the photoacoustic diagnosis.

Further features of the present invention will become apparent from the following description of exemplary embodiments with reference to the attached drawings.

DESCRIPTION OF EMBODIMENTS

Preferred embodiments of the present invention will now be described with reference to the drawings. The dimensions, materials, shapes, relative arrangements or the like of the composing elements to be described hereinbelow should be changed appropriately depending on the configuration and the various conditions of the apparatus to which the invention is applied, and are not intended to limit the scope of the invention to the following description.

An object information acquiring apparatus of the present invention is an apparatus that utilizes the photoacoustic effect, in concrete terms, an acoustic wave which is generated by irradiating the light (electromagnetic wave) onto an object and is propagated in the object, is received, whereby object information, which is characteristic information on the object, is acquired as image data. The acquired object information is characteristic information to indicate the generation source distribution of an acoustic wave generated by light irradiation, the initial sound pressure distribution in the object, the light energy absorption density distribution and the absorption coefficient distribution that are derived from the initial sound pressure distribution, and the concentration distribution of a substance which constitutes a tissue, for example. The substance which constitutes a tissue is, for example, blood components indicated in the oxygen saturation distribution and in the oxyhemoglobin/deoxyhemoglobin concentration distribution, lipids, collagen or water.

The acoustic wave in the present invention is typically an ultrasound wave, including an elastic wave called sound wave and acoustic wave. An acoustic wave generated by the photoacoustic effect is called a "photoacoustic wave" or a "light-induced ultrasound wave". The apparatus of the present invention receives an acoustic wave which is generated or reflected in an object, and is propagated therefrom, using such an acoustic wave detector as a probe.

The present invention can be applied to a photoacoustic diagnostic apparatus that generates image data by analyzing a photoacoustic wave and allows diagnosis based on the image. In the following description, such a photoacoustic diagnostic apparatus will be described as a typical example of the object information acquiring apparatus. The present invention can also be understood as a control method of the object information acquiring apparatus, and a program that allows an information processor to execute this control method.

Basic Embodiment

Figure 1:
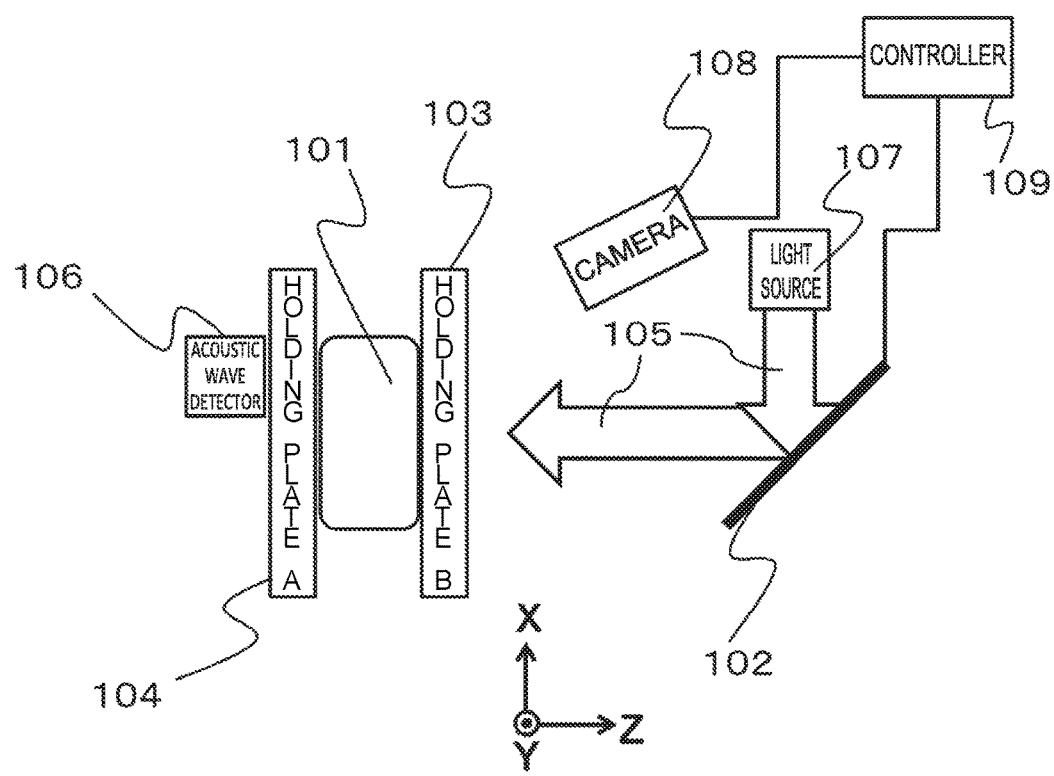
FIG. 1 is a diagram depicting an apparatus configuration and light irradiation control.

A basic embodiment of the present invention will now be described. Control of the light irradiation position, which is a characteristic of the present invention, will be described with reference to FIG. 1. In FIG. 1, the Z axis direction is the horizontal direction on the paper surface, the Y axis direction is the direction perpendicular to the paper surface, and the X direction is the vertical direction on the paper surface.

An apparatus illustrated in FIG. 1 includes a controlling member 102, a holding plate A (104), a holding plate B (103), an acoustic wave detector 106, a light source 107 that irradiates pulsed light 105, a camera 108 and a controller 109. A measurement target of this apparatus is an object 101 which directly or indirectly contacts the holding plate A (104) and the holding plate B (103).

The pulsed light 105 emitted from the light source 107 reaches the controlling member 102 that controls the light irradiation area via an optical system (not illustrated), such as a mirror and optical fiber. For the controlling member 102, a digital mirror device (DMD), a transmission type liquid crystal element or a reflection liquid crystal element, for example, can be used. A reflection type liquid crystal element that uses a semiconductor substrate, in particular, is called "liquid crystal on silicon" (LOCS). As this example shows, an element used for a standard data projector can be suitably used as a material of the controlling member 102. The controlling member 102 plays a role of blocking light irradiated onto an area other than the object, in order to solve the noise generation problem mentioned above.

The camera 108 is a video capture camera that observes (images) an object. The controller 109 has both a function to acquire a camera image and a function to control the controlling member 102. Thereby the controller 109 recognizes the shape of the object 101, and the pulsed light 105, controlled to be irradiated onto only a predetermined area, is irradiated onto the object 101.

The acoustic wave detector 106 receives an acoustic wave generated from a light absorber inside the object 101 onto which the pulsed light 105 is irradiated. If the acoustic wave detector 106 is compact, that is, if the area of a reception surface of the acoustic wave detector 106 is smaller than an area on the holding plate B (104) where the object 101 is projected, the acoustic wave detector 106 should be scanned in the XY directions, so that the photoacoustic wave is received at each position.

In the same manner, if the light irradiation range by the light source 107 is small, the entire object 101 can be irradiated by the pulsed light 105 if the optical system (in particular, light emission end) is scanned in the XY directions.

During this scanning, if the acoustic wave detector 106 or the pulsed light 105 moves outside an area on the holding plate B (104) where the object 101 is orthogonally projected, the object 101 does not exist between the optical system and the acoustic wave detector 106. In this state, light is directly irradiated onto the acoustic wave detector 106, and noise is generated.

In the present invention, however, the light irradation area is controlled by the controlling member 102, hence the pulsed light irradiated from the light source 107 is never directly irradiated onto the acoustic wave detector 106. Therefore the influence of noise can be eliminated.

In this embodiment and in the later mentioned embodiments, a concrete method to control the light irradiation area will be described hereinbelow. To describe the basic concept, a method of automatically performing irradiation control will be described in this embodiment.

Figure 2:
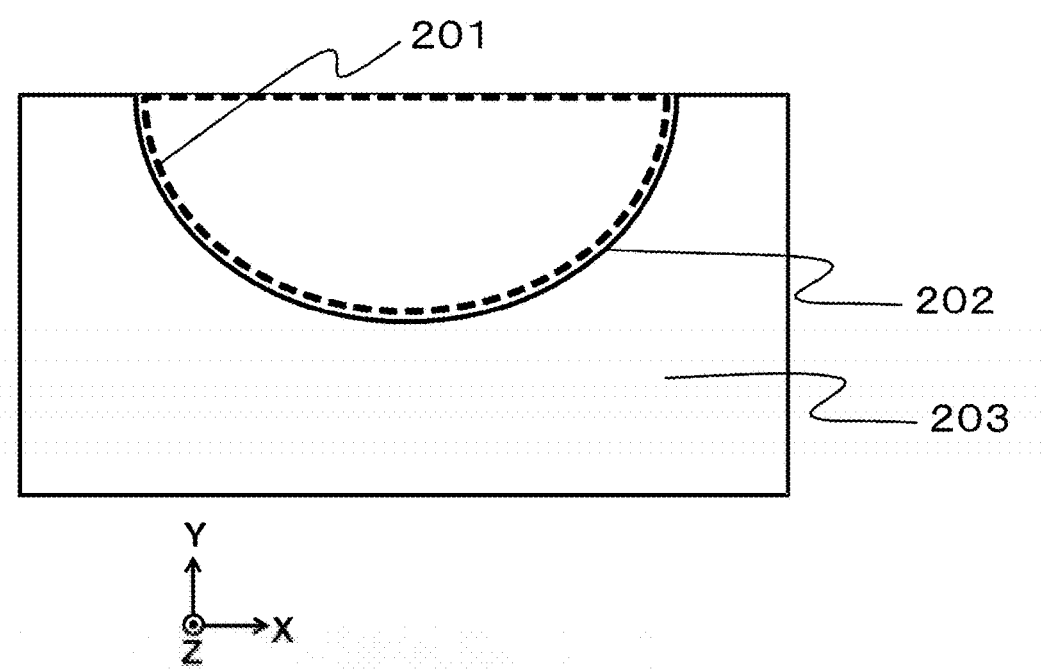
FIG. 2 is a diagram depicting a light irradiation area on an object.

FIG. 2 is a diagram depicting a state when the pulsed light is irradiated in the Z axis direction from the front side to the back side of the paper surface, and the acoustic wave detection is located on the back side of the paper surface. The object (solid line contour 202) held by the holding plate 203 is imaged as shown in FIG. 2 by the camera 108 shown in FIG. 1. Here in the area where the object exists, the contour of the object can be automatically extracted by a known method, such as an edge extraction method. The controller controls such that light is irradiated only onto an area inside the contour of the object acquired here. Particularly when the optical system (emission end) is scanned, the controller controls such that the shape of the light irradiation is changed according to the light irradiation position.

For control, it is preferable to set a small margin to prevent the light from directly reaching the acoustic wave detector. In concrete terms, it is controlled such that a slightly inner side of the extracted contour 202 is irradiated, as indicated by the dotted line 201 in FIG. 2.

Figures 3A, 3B, 3C, 3D, 3E, 3F, 3G, 3H, 3I, 3J:
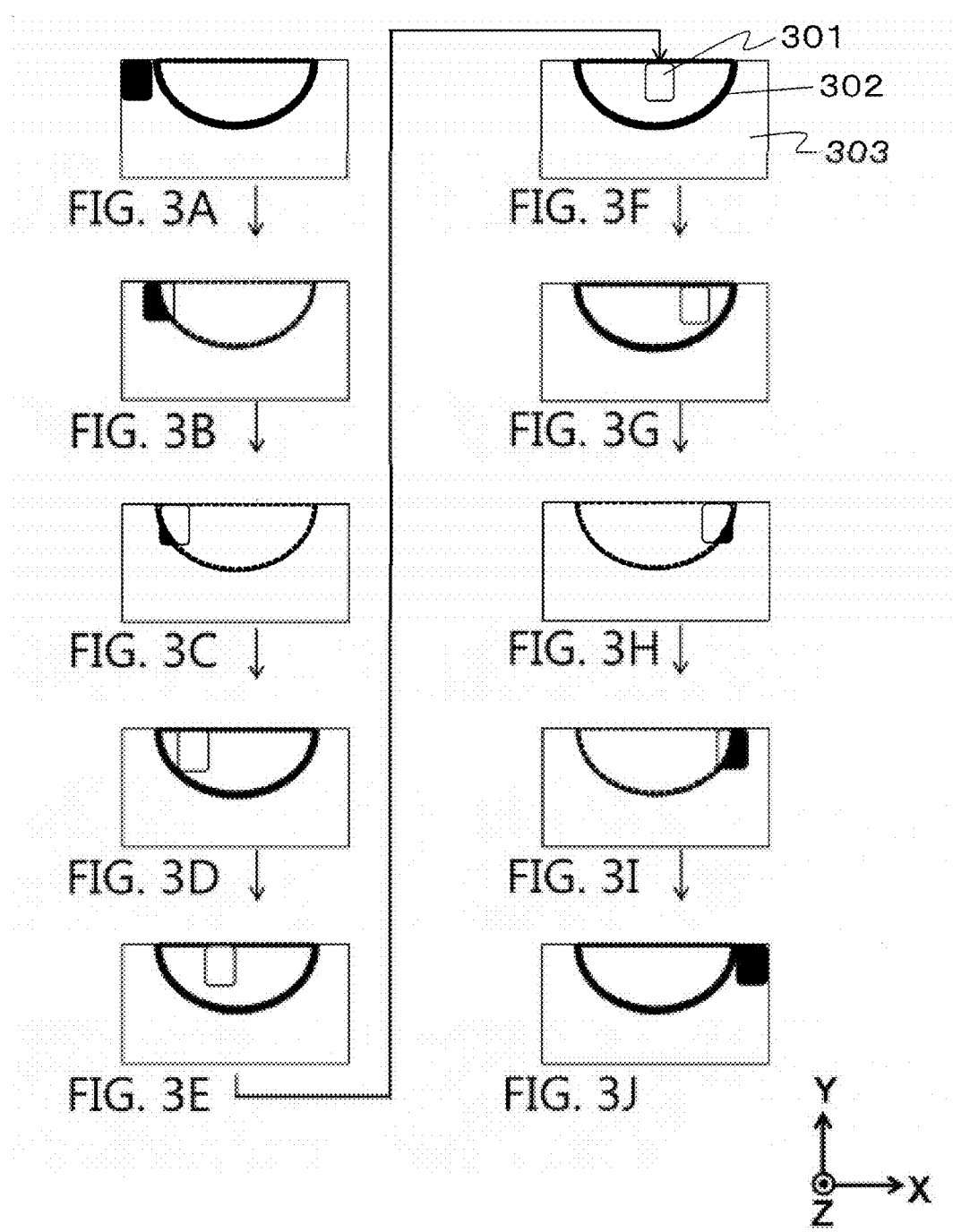
FIG. 3A to FIG. 3J show the scanning state in light irradiation.

FIG. 3 shows the emission end of the pulsed light and a state of irradiating light while scanning the acoustic wave detector in a time series. Here it is assumed that scanning is performed while constantly maintaining the positions of the pulsed light irradiation position and the acoustic wave detector that face each other. As illustrated in FIG. 3A and FIG. 3J, the light irradiation area 301 is scanned in the X axis direction. The acoustic wave detector, which is disposed facing the light irradiation area 301, is also scanned in the same manner.

In FIG. 3A, the light irradiation area 301 is located outside the orthogonal projection area of the object 302 that is held by the holding plate 303. Therefore the controller controls the controlling member 102 so as to turn the light irradiation to the entire surface OFF. Thereby direct irradiation of the pulsed light onto the acoustic wave detector is prevented.

In FIG. 3B, it is controlled so that light is irradiated only onto a partial area where the object exists, and light is not irradiated onto the rest of the area where the object does not exist. In FIG. 3C as well, a part of the area exists outside the object, and it is controlled so that light is not irradiated onto this area.

In FIG. 3D to FIG. 3G, the light irradiation area is inside the object, hence the pulsed light is not directly irradiated onto the acoustic wave detector. Therefore it is controlled so that light is irradiated onto the entire surface of the object.

In FIG. 3H and FIG. 3I, a part of the area exists outside the object again, and it is controlled so that light is not irradiated onto this area.

In FIG. 3J, the entire light irradiation area is located outside the object. Therefore irradiation is controlled so as to turn the light irradiation onto the entire surface of the element of the controlling member 102 OFF, to prevent direct irradiation of the pulsed light onto the acoustic wave detector.

By this control, light is irradiated only onto the object, and is never irradiated onto an area other than the object, hence directly irradiating light onto the acoustic wave detector can be prevented.

Figure 4:
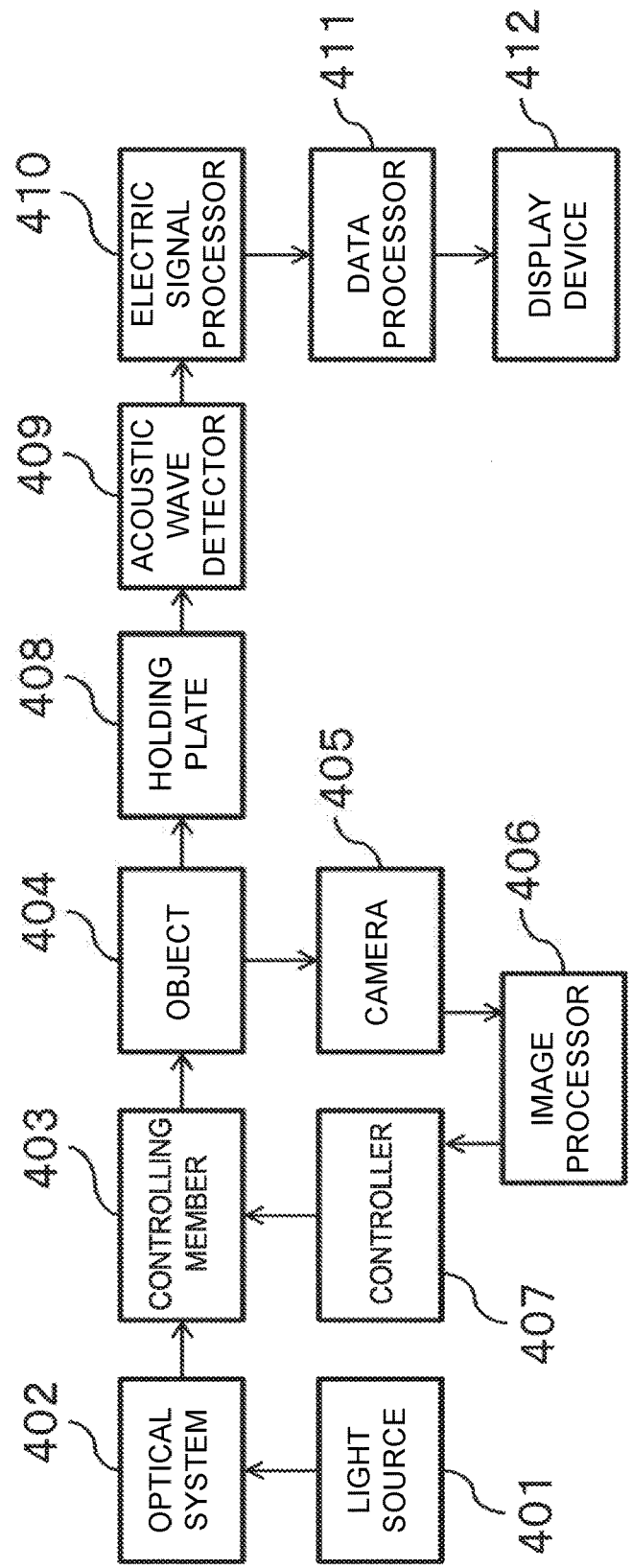
FIG. 4 is a block diagram depicting the composing elements of the apparatus.

Now the composing elements of this embodiment will be described. FIG. 4 is a block diagram depicting the composing elements of this embodiment. The photoacoustic diagnostic apparatus is constituted by a light source 401, an optical system 402, a controlling member 403, a camera 405, an image processor 406, a controller 407, a holding plate 408, an acoustic wave detector 409, an electric signal processor 410, a data processor 411 and a display device 412. The measurement target of the apparatus is an object 404.

(Light Source)

The light source 401 generates pulsed light. Laser is preferable for the light source because high power can be obtained, but a pulsed light source, such as a light emitting diode and a xenon lamp may be used. To effectively generate a photoacoustic wave, light must be irradiated for a sufficiently short time according to the thermal characteristic of an object. If the object is an organism, the pulse width of the pulsed light that is generated by the light source 401 is preferably several tens of nanoseconds or less. The wavelength of the pulsed light is preferably in a near infrared region called the "in vivo window", which is about 700 nm to 1200 nm. The light in this region can reach a relatively deep area of an organism, whereby information on the deep area can be acquired. If measurement is limited to only the surface area of an organism, the visible light (about 500 nm to 700 nm) to the near infrared region may be used. The wavelength of the pulsed light is appropriately set considering various conditions, such as the "absorption coefficient of the object to be measured must be higher than the absorption coefficient of the background" in accordance with the observation target.

(Optical System)

The optical system 402 guides the pulsed light generated by the light source 401 to the controlling member 403 and the object 404. In concrete terms, the optical system 402 includes such optical components as an optical fiber, a lens, a mirror and a diffusion plate. In some cases, the irradiation shape and the light density of the pulsed light may be changed using these optical components. The optical components are not limited to those mentioned here. Any optical system may be used if only the light having a predetermined shape and density can be irradiated onto the object.

As mentioned above, an element used for a standard data projector can be used for the control member, therefore an optical system for a projector can be used for the optical system mentioned here.

(Controlling Member)

The controlling member 403 controls the light irradiation area based on the later mentioned video capture image. The principle is the same as that of a light valve used for a data projector, and if a desired area is set, light is irradiated only onto this area and not irradiated onto the other areas. For the controlling member 403, a DMD, a transmission liquid crystal element or a reflection type liquid crystal element, such as LCOS, can be used.

(Object)

The object 404 is a measurement target. For the object, an organism or a phantom simulating acoustic characteristic and optical characteristic of an organism is used. In the photoacoustic diagnostic apparatus, a light absorber which has a large light absorption coefficient, located inside the object, is imaged. If the object is an organism, the imaging target is, for example, hemoglobin, water, melanin, collagen or lipids. In the case when the object is a phantom, a substance simulating the optical characteristics of the imaging target is enclosed inside as the light absorber. In an organism, there are individual based differences in shape and characteristics.

(Camera)

The camera 405 observes and measures an external shape of an object. To accurately determine the light irradiation area, it is preferable to align the light irradiation direction and the imaging direction of the camera as much as possible. If these directions cannot be aligned, the light irradiation area may be calculated considering the installation angle, the angle of view or the like of the camera.

(Image Processor)

The image processor 406 extracts a contour of the object from an image acquired by the camera 405, and detects an area where the light should be irradiated. For the contour extraction, a known edge extraction technique can be used.

As mentioned above, if the imaging direction of the camera is not aligned to the irradiation direction of the pulsed light, the light irradiation area cannot be correctly controlled. Therefore this apparatus includes a calculation algorithm to correct the misalignment. Further, this apparatus also includes an algorithm to set a margin, considering the calculation error or the diffusion of light irradiated from the optical system to the object, that is, an algorithm to set a light irradiation area in an area different from the extracted contour. The algorithm may be included as a program, which is stored in a storage device and executed by a CPU or the like.

(Controller)

The controller 407 controls the state of the controlling member 403 based on the operation result of the image processor 406. If a display device is used for a projector of DMD or LCOS as the controlling member 403, then a device equivalent to a standard display driver can be used as the controller 407.

(Holding Plate)

The holding plate 408 is a member to stably hold an object. At the same time, the holding plate 408 may be used for decreasing the thickness of the object by pressurizing the object, so that the deep area inside the organism is measured during photoacoustic diagnosis. In this embodiment, it is assumed that an object is held by two holding plates, but an object may be held by three or more holding plates. As a base on which an object is placed, only one plate may be used, and this plate used as the base is also included in the holding plate of the present invention.

In the case when two holding plates are used and one of the holding plates (called "holding plate B") exists between the acoustic wave detector and an object, it is preferable to use a material for the holding plates by which an acoustic wave generated from the object does not attenuate very much. Such a resin as acrylic and PET can be used, and polymethylpentene (product name: TPX) can be suitably used as well.

For the other holding plate (called "holding plate A") which does not need to have a function to propagate the acoustic wave, any material, including glass and resin, may be used. However if light emitted from the optical system is irradiated onto the object through this holding plate A, it is preferable to use a material that is highly light transmissive.

(Acoustic Wave Detector)

The acoustic wave detector 409 converts an acoustic wave into an electric signal. A single acoustic wave detector may be moved to a plurality of locations by scanning or a plurality of photoacoustic detectors may be installed in different locations. If a plurality of reception elements that convert an acoustic wave into an analog elastic signal is one dimensionally or two dimensionally arranged, the measurement time can be decreased, and improvement of the SN ratio can be expected.

When an acoustic wave generated inside the object 404 is received by the acoustic wave detector 409, the acoustic wave detector 409 must be installed to acoustically couple with the object 404 in order to suppress reflection and attenuation of the generated acoustic wave. Therefore it is preferable to dispose an acoustic matching material, such as acoustic matching gel, water and oil, between the acoustic wave detector 409 and the object 404. If the acoustic wave detector 409 contacts the object via the holding plate B, the acoustic matching material is disposed between the acoustic wave detector 409 and the holding plate.

It is preferable that the acoustic wave detector 409 has high sensitivity and a wide frequency band. For example, an acoustic wave detector 409 using PZT, PVDF, cMUT or a Fabry-Perot interferometer, can be used.

(Electric Signal Processor)

The electric signal processor 410 amplifies an analog electric signal acquired by the acoustic wave detector 409, and converts the analog electric signal into a digital signal. In order to efficiently acquire data, it is preferable to have a same number of analog-digital converters (ADCs) as a number of reception elements of the acoustic wave detector 409. However one ADC may be switched and used by time-division.

(Data Processor)

The data processor 411 processes the digital signal acquired by the electric signal processor 410, and reconstructs image data. In concrete terms, a computer, an electric circuit or the like is used as the data processor 411. For this processing method, any method that can reconstruct an image can be used, including a universal back projection method that superimposes differentiated signals.

(Display Device)

The display device 412 displays image data generated by the data processor 411. In concrete terms, a display of a computer, a TV or the like can be used.

Figure 5:
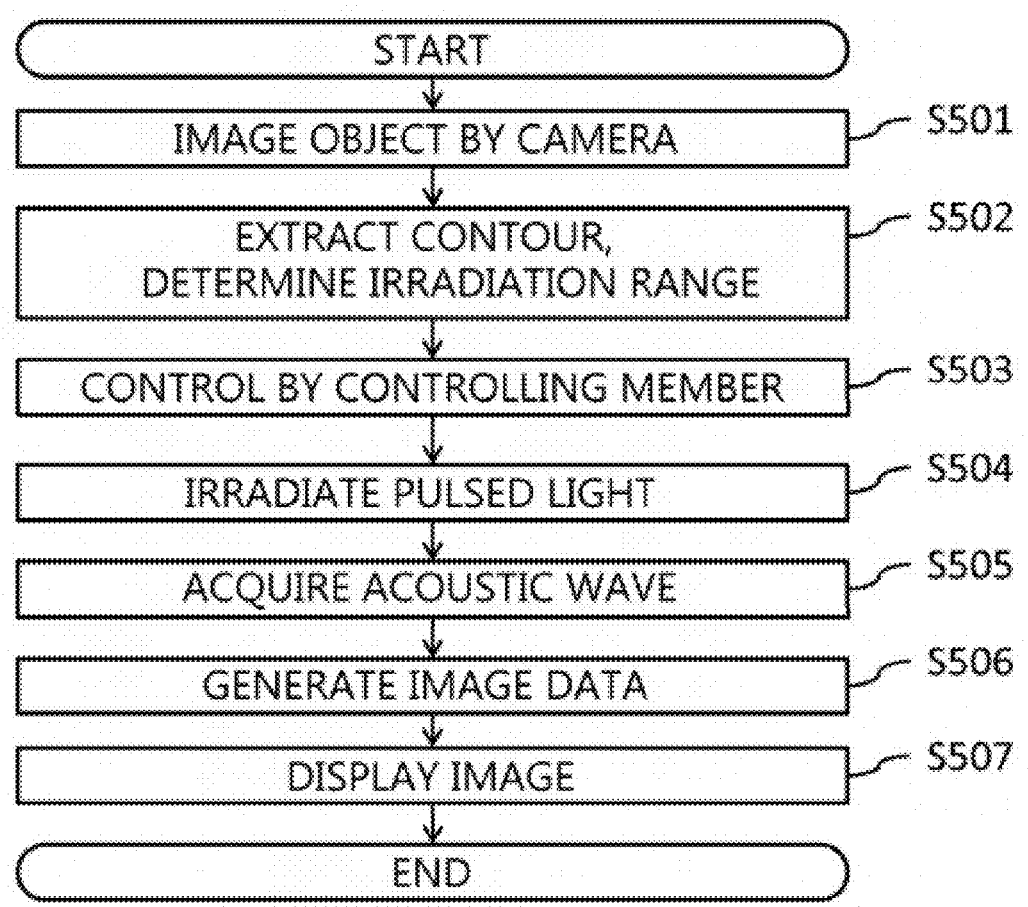
FIG. 5 is a flow chart depicting an operation of the apparatus.

Now the operation flow of this apparatus will be described with reference to FIG. 5. Before operating this apparatus, an object is set in the apparatus, and then a controlling member and the like are set at appropriate positions. This apparatus is started when the preparation for measuring the object completes in this way.

First in step S501, an image of the object is captured by the camera.

In step S502, the image processor processes this captured image and extracts the contour, and determines the irradiation range of the pulsed light.

In step S503, the control member is controlled in advance based on this information.

When control completes, the pulsed light is irradiated from the light source in step S504.

In step S505, the acoustic wave detector acquires the acoustic wave generated by the photoacoustic effect. At this time, the light is irradiated only onto the object because of the control performed in step S503, hence the photoacoustic wave is not generated from the acoustic wave detector.

In step S506, the data processor processes a digital signal originated from the acquired acoustic wave, and generates image data based on the characteristic information inside the object.

In step S507, the display device displays the image inside the object based on the image data.

According to this processing flow, the acoustic wave is not generated on the surface of the acoustic wave detector, therefore noise on the signal can be removed, and image quality of the image can be improved.

Embodiment 2

In the above mentioned basic embodiment, the light irradiation range is determined based on the result of processing the camera image by the image processor. In Embodiment 2, the light irradiation range is set manually.

The photoacoustic diagnostic apparatus according to this embodiment includes an input device that allows a user (medical staff, operator) to set a desired range while checking the image displayed on the display device, in addition to the configuration in FIG. 4. For the input device, a mouse, pen tablet, touch panel or the like can be used. Coordinates may be displayed with an image, so that the user can input numeric values. In this embodiment, an image captured by the camera is displayed on the display device. The user specifies a desired light irradiation range using the input device while checking the image.

By irradiating light based on the specified area, a good image with little noise can be acquired without directly irradiating light onto the acoustic wave detector.

Embodiment 3

In the above mentioned embodiments, a configuration for controlling the irradiation area is used, that is, a configuration similar to that of the data projector is used for the controlling member and the optical system. In Embodiment 3, a technique applying direct viewing LCD technology will be described.

Figure 6:
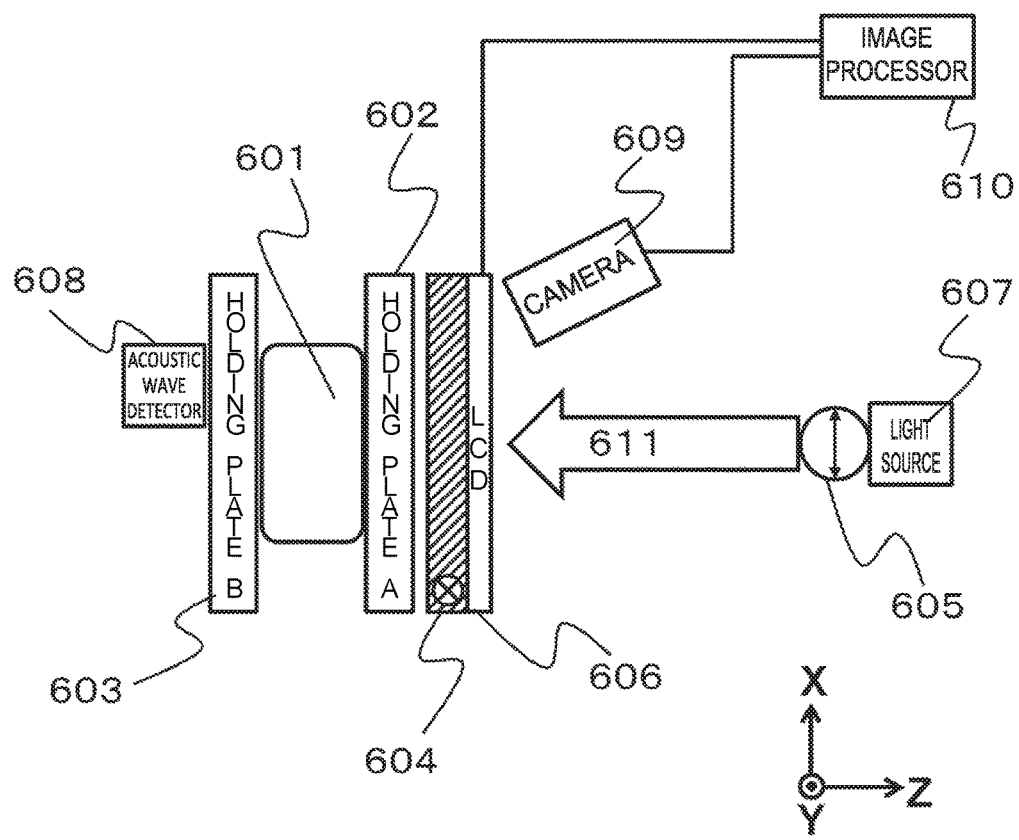
FIG. 6 is a diagram depicting an apparatus configuration and a light irradiation control according to Embodiment 3.

FIG. 6 shows a configuration of the apparatus. A liquid crystal display 606, which is a characteristic composing element of this embodiment, is a panel itself, which does not include a polarizing plate, of all liquid crystal displays used for personal computers, flat panel TVs or the like. The reference symbol 604 indicates a polarizing plate, of which absorption axis in the Y axis direction. The reference symbol 605 also indicates a polarizing plate, of which absorption axis is in the X axis direction.

The other composing elements are the same as a basic embodiment. In other words, the holding plate A (602) and the holding plate B (603) hold the object 601 stably. The image processor 610 calculates a predetermined light irradiation area to which the pulsed light 611 is irradiated from the light source 607, based on the image of the object 601 captured by the camera 609, and transfers the light irradiation area to the liquid crystal display 606. Thereby the pulsed light 611 can be controlled so as not to be directly irradiated onto the acoustic wave detector 608.

In this embodiment, the irradiation area control can be implemented by using a configuration of a standard liquid crystal display as well, where the liquid crystal display 606 is sandwiched by the polarizing plates 604 and 605, for example. However separating the polarizing plates, as in the case of this embodiment, is more preferable for the following reasons.

A first reason is that the liquid crystal display in a standard configuration is slightly darker in terms of light utilization efficiency.

A second reason is that if an irradiation area is determined and the liquid crystal display 606 is controlled accordingly, the outside of the contour of the object 601 is completely shielded from light, and cannot be observed even with the camera 609. Therefore a slight abnormality in the peripheral area of the object cannot be monitored. If the polarizing plates are separated as in the case of this embodiment, even in an area where the pulsed light 611 is not irradiated, the measured state can be monitored by the camera 609.

Thus a good image with little noise can also be acquired by the configuration of this embodiment.

Embodiment 4

The above mentioned embodiments, which use data projection technology and direct viewing displays, such as a liquid crystal TV, are on the one hand simple and highly accurate, but cost is somewhat high. Further a matrix substrate is used, where the aperture ratio is not always 100%, which makes it insufficient to utilize pulsed light effectively.

Therefore in this embodiment, a configuration of which cost is lower and light utilization efficiency is high is disclosed. Compared with Embodiment 3 shown in FIG. 6, this embodiment has a similar configuration, but a difference is that λ/2 plates are cut into rectangular shapes and inserted from both sides of the object, instead of using a liquid crystal display.

Figure 7:
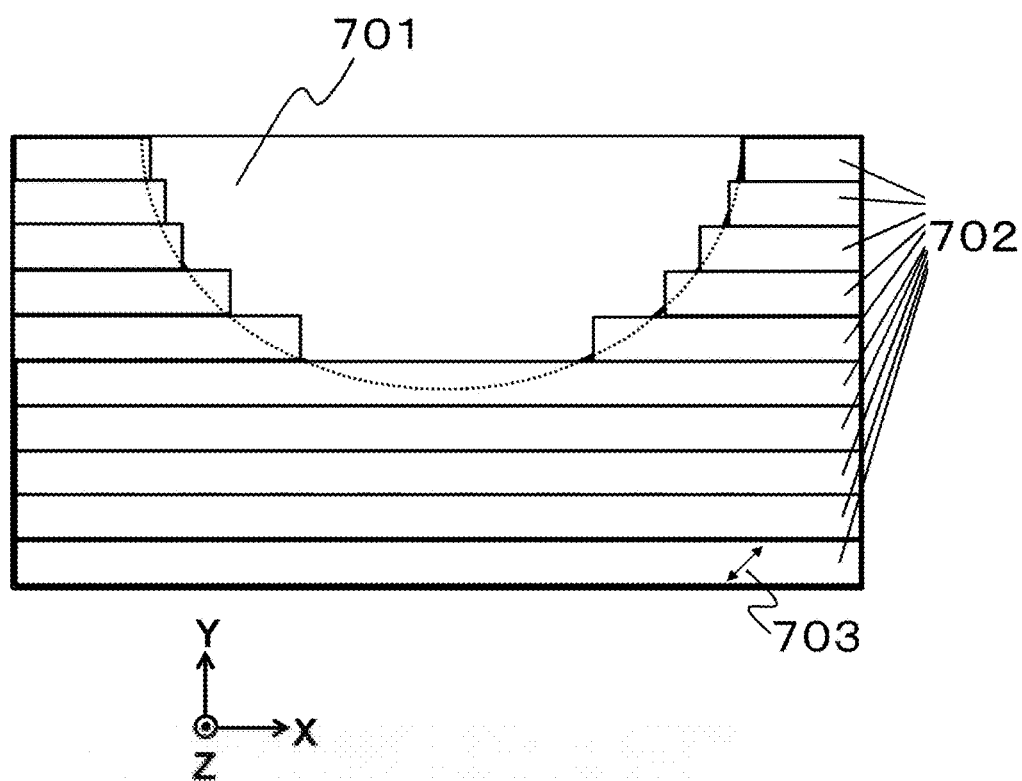
FIG. 7 is a diagram depicting an arrangement of $\lambda/2$ plates according to Embodiment 4.

FIG. 7 is a diagram depicting the configuration of this embodiment viewed in the Z axis direction in FIG. 6. In sequence from the backside to the front side of the paper surface, a holding plate B (not illustrated), an object 701, a holding plate A (not illustrated), a polarizing plate (not illustrated) and λ/2 plates 702 are disposed.

If the absorption axes of the polarizing plates are the X axis and the Y axis as shown in FIG. 6, the optical axes of the λ/2 plates are preferably set to a 45° direction from the X axis, as indicated by the reference symbol 703. This can suppress the light irradiation onto the acoustic wave detector, in the same manner as in Embodiment 3. Monitoring of the object by camera is also possible.

Thus by the configuration of this embodiment as well, a good image with little noise can be acquired.

Example

An example to demonstrate an effect of the present invention, when the basic embodiment mentioned above is adopted, will be described with reference to FIG. 8.

An object used in this example is a semispherical phantom, and the acoustic characteristics and the optical characteristics of the phantom base material are similar to those of an organism. Inside the phantom, light absorbers 801 are installed in positions located about 5 mm from the surface. The light absorption coefficient of the light absorber is assumed to be about five times that of the phantom base material. Each of the two polymethylpentene plates having a 10 mm thickness is disposed on both sides of the object as holding plates, so as to be in contact with the object respectively, and a 1 mm thick oil layer is disposed behind one of the holding plates, and the acoustic wave detector is contacted with the holding plate via this oil layer. Castor oil is used for this oil layer. For the element of the acoustic wave detector, PZT of which diameter of the reception unit is 2 mm, and the central frequency is 1 MHz with an 80% band width utilization, is used. This element is disposed as an 18×18 array in the plane direction to constitute one acoustic wave detector. The acoustic detector is connected to the XY stage, so as to scan the surface of the object while turning the reception surface, where the reception elements are arrayed, toward the object.

For the camera to monitor the object, a CCD camera (5,000,000 pixels) is used. Thereby the state during measurement can be observed.

A light source used here is a pulsed light source that generates a nanosecond order pulsed light (wavelength: 1064 nm) using an Nd:YAG laser. The light source irradiates pulsed light onto the object via DMD from a surface opposite the acoustic wave detector. The irradiation area on the object can be adjusted by controlling the DMD using a dedicated display driver. This optical system is connected to the XY stage, and can scan the object in the XY directions in sync with the acoustic wave detector.

The image processor performs edge extraction on the image captured by the CCD camera, and determines an area 5 mm inside the edge as the light irradiation area. Thereby light irradiation onto the acoustic wave detector can be suppressed. Based on the information on the light irradiation area, the controller controls the display driver for DMD, and detects the pulsed light irradiation area for each location scanned in the XY directions. According to this control information, the light irradiation, the reception of the acoustic wave and the XY scanning are repeated in each location on the object, whereby data on the entire area of the object can be acquired. The ADC to be used has a 20 MHz sampling frequency and a 12-bit resolution. Three-dimensional image data can be acquired by the data processor reconstructing the digital signal by a back projection method.

In this example, for purposes of comparison, a similar measurement is performed in a state where the light is also irradiated onto the acoustic wave detector by controlling the display driver for the DMD as appropriate.

Figure 8A:
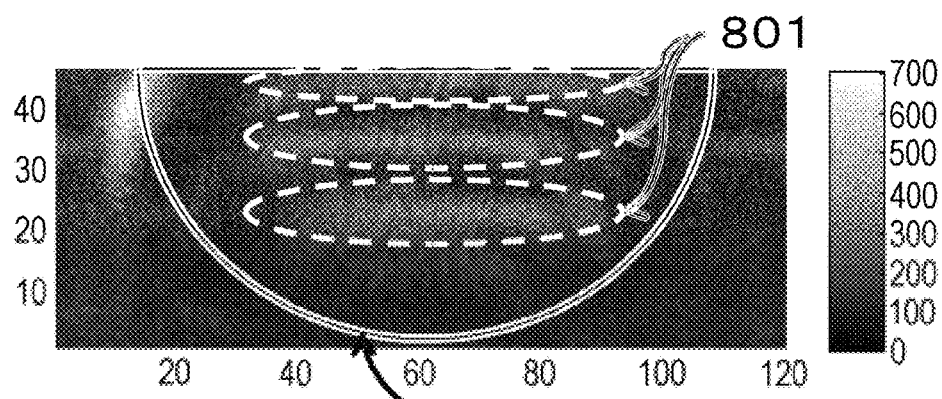
FIG. 8A and FIG. 8B show images that are displayed.
Figure 8B:
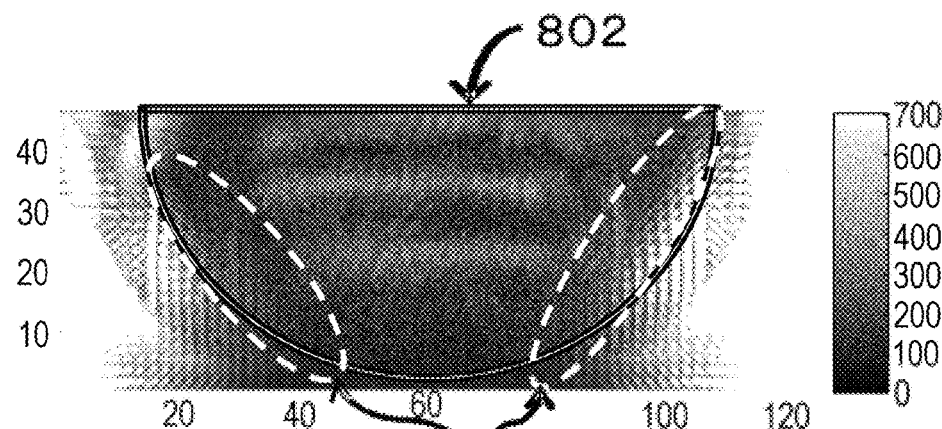

FIG. 8A shows an image when the present invention is applied, that is, an image acquired when light is not irradiated onto areas other than the object by DMD. FIG. 8B, on the other hand, shows an image when light is irradiated onto areas other than the object (acoustic wave detector). This image is a maximum intensity projection (MIP) diagram of three-dimensional image data.

In FIG. 8B, three light absorbers disposed inside the phantom are visible, but considerable noise is generated, as indicated by the broken line 803, outside the contour 802 of the object. This noise even enters inside the object, which is not desirable for diagnosis.

In the case of FIG. 8A, noise outside the contour of the object is not generated, and the light absorbers are displayed. The signal-to-noise ratio of the light absorber portions is 2.8 in FIG. 8B, but is 4.2 in FIG. 8A, indicating an improvement of image quality.

As described above, the present invention can suppress the generation of noise and provide an image having high image quality.

High quality images similar to this example can also be acquired by acquiring images according to Embodiment 2 to 4.

The present invention was described using linearly polarized light, but similar effects can also be acquired by using circularly polarized light or elliptically polarized light, and by using polarizing plates appropriately designed corresponding to the polarized light.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-064511, filed on Mar. 26, 2013, which is hereby incorporated by reference herein in its entirety.

The invention claimed is:

1. An object information acquiring apparatus comprising:
a light source configured to generate light;
a controller configured to control a shape of an irradiation area of the light;
a controlling member configured to limit the irradiation area based on an instruction from said controller;
a detector configured to receive an acoustic wave generated from an object which is irradiated with the light;
a processor configured to generate characteristic information about a region inside the object using the acoustic wave received by said detector; and
an acquirer configured to acquire a shape of the object,
wherein said controller controls said shape of said irradiation area based on the shape of the object acquired by said acquirer so as to prevent said detector from being irradiated with the light without passing through the object, and
wherein said controlling member includes at least any one of a digital mirror device, a reflection type liquid crystal element, a transmission type liquid crystal element and a $\lambda/2$ plate.

2. The object information acquiring apparatus according to claim 1, further comprising a holding unit that holds the object,
wherein said detector receives the acoustic wave from the object via said holding unit, and
said controller suppresses irradiation of light onto said detector outside an area on said holding unit where the object receives light orthogonally projected onto the object.

3. The object information acquiring apparatus according to claim 2, wherein said detector is acoustically coupled to the object via said holding unit interposed between said detector and the object, and receives an acoustic wave while scanning said holding unit.

4. The object information acquiring apparatus according to claim 2, wherein said acquirer is a camera that images the object contacting said holding unit.

5. The object information acquiring apparatus according to claim 4, wherein said controller detects a contour of the object by processing an image captured by said acquirer, and controls the irradiation area based on the contour.

6. The object information acquiring apparatus according to claim 4, further comprising a display unit that displays an image captured by said acquirer, and an input unit that receives input from an operator,
wherein said controller controls the irradiation area based on information that the operator inputted based on an image displayed on said display unit.

7. The object information acquiring apparatus according to claim 1, wherein said processor generates image data about the region inside the object by reconstruction based on the characteristic information.

8. The object information acquiring apparatus according to claim 1, further comprising a scanner configured to move the light from the light source,
wherein said controller controls an irradiation spot of the light in associated with a position of the light so as to define the shape of the irradiation area.

9. The object information acquiring apparatus according to claim 8, wherein the scanner moves the detector and the light source synchronously.

10. The object information acquiring apparatus according to claim 8, wherein the scanner includes a two dimensional stage which moves the irradiation spot of the light in two dimensional manner.

11. A control method of an object information acquiring apparatus including a light source, a controller configured to control irradiation of light from the light source, a detector, a processor and an acquirer, the control method comprising:
a step of the acquirer acquiring the shape of an object;
a step of the controller controlling an irradiation area when the object is irradiated with light from the light source, based on a shape of the object acquired by the acquirer;
a step of the detector receiving an acoustic wave generated from the object which is irradiated with light from the light source; and
a step of the processor generating characteristic information about a region inside the object using the acoustic wave received by the detector,
wherein said step of controlling an irradiation area is performed such that said shape of said irradiation area is limited by using an area masking device based on the shape of the object acquired by said acquirer so as to prevent said detector from being irradiated with the light without passing through the object, and
wherein said area masking device includes at least any one of a digital mirror device, a reflection type liquid crystal element, a transmission type liquid crystal element and a $\lambda/2$ plate.

* * * * *